United States Patent
DeRose et al.

(10) Patent No.: US 8,947,764 B1
(45) Date of Patent: Feb. 3, 2015

(54) HIGH-SPEED PHOTONIC MODULATOR DESIGNS

(71) Applicant: Sandia Corporation, Albuquerque, NM (US)

(72) Inventors: Christopher DeRose, Albuquerque, NM (US); William A. Zortman, Corrales, NM (US)

(73) Assignee: Sandia Corporation, Albuquerque, NM (US)

( * ) Notice: Subject to any disclaimer, the term of this patent is extended or adjusted under 35 U.S.C. 154(b) by 190 days.

(21) Appl. No.: 13/860,978

(22) Filed: Apr. 11, 2013

Related U.S. Application Data

(60) Provisional application No. 61/622,596, filed on Apr. 11, 2012.

(51) Int. Cl.
   *G02F 1/29* (2006.01)
   *G02F 1/035* (2006.01)

(52) U.S. Cl.
   CPC .................................. *G02F 1/29* (2013.01)
   USPC .............................................. 359/315; 385/2

(58) Field of Classification Search
   CPC ........................................................ G02F 1/29
   USPC ..................................... 359/315; 385/2, 9, 14
   See application file for complete search history.

(56) References Cited

U.S. PATENT DOCUMENTS

2008/0056636 A1 * 3/2008 Shih et al. ......................... 385/2

\* cited by examiner

*Primary Examiner* — William Choi
(74) *Attorney, Agent, or Firm* — Martin I. Finston

(57) ABSTRACT

An optical device includes a microdisk optical resonator element. The microdisk resonator element is formed on a substrate and has upper and lower portions respectively distal and proximal the substrate. An arcuate semiconductor contact region partially surrounds the microdisk resonator element. A first modulator electrode is centrally formed on the upper portion of the microdisk resonator element, and a second modulator electrode is formed on the arcuate contact region. A laminar semiconductor region smaller in thickness than the microdisk resonator element separates the arcuate contact region from the microdisk resonator element and is formed on the substrate so as to electrically connect the arcuate contact region to the lower portion of the microdisk resonator element.

6 Claims, 3 Drawing Sheets

HIGH-SPEED PHOTONIC MODULATOR DESIGNS

CROSS-REFERENCE TO RELATED APPLICATIONS

This application claims the benefit of U.S. Provisional Application Ser. No. 61/622,596 entitled HIGH-SPEED PHOTONIC MODULATOR DESIGNS and filed on Apr. 11, 2012, which application is incorporated by reference in its entirety.

STATEMENT OF GOVERNMENT INTEREST

This invention was developed under Contract DE-AC04-94AL85000 between Sandia Corporation and the U.S. Department of Energy. The U.S. Government has certain rights in this invention.

TECHNICAL FIELD

The present invention is directed generally to high-speed photonic modulator designs, and, more particularly, to resonant modulators such as those in disk and ring geometries.

BACKGROUND OF THE INVENTION

One type of optical modulator that has promise for high-speed applications such as exascale computing and next generation optical communications is the resonant optical modulator. A resonant optical modulator includes an optical resonator that is typically a waveguiding ring or disk of silicon, although other geometries and other materials are not excluded. An input and output optical beam is coupled to the resonator by directing the beam through a waveguide, which may e.g. be a rectilinear planar waveguide, situated within an evanescent coupling distance of the resonator.

Within a characteristic wavelength band, such a modulator is relatively transmissive when light coupled into the modulator excites a resonant mode of the resonator, and is less transmissive when it goes out of resonance with the coupled light. The resonance may be controlled by, e.g., thermal or electronic modification of the optical velocity within the resonator.

One of the advantages of resonant modulators relative to competing technologies is that they occupy a relatively small volume, and as a consequence are conservative as to wafer real estate and as to power demands. Because the design of such modulators is a relatively new field, there remain opportunities for further improving their performance.

SUMMARY OF THE INVENTION

An exemplary embodiment of the present invention is a photonic modulator including a disk resonator and modulator electrodes. In contrast to more conventional designs in which both modulator electrodes are defined in a central portion of the device, one of the modulator electrodes is moved to the periphery of the inventive device. By this means, the series resistance between the modulator electrodes can be reduced, thereby increasing the operating radiofrequency bandwidth of the device.

Accordingly, the present invention in one aspect is an optical device including a microdisk optical resonator element. (By "microdisk resonator element" is meant an element that operates, at least in part but necessarily in entirety, as a microdisk optical resonator.) The microdisk resonator element is formed on a substrate and has upper and lower portions respectively distal and proximal the substrate. An arcuate, i.e. arc-shaped but not covering an entire 360 degrees, semiconductor contact region partially surrounds the microdisk resonator element. A first modulator electrode is centrally formed on the upper portion of the microdisk resonator element, and a second modulator electrode is formed on the arcuate contact region. A laminar semiconductor region smaller in thickness than the microdisk resonator element separates the arcuate contact region from the microdisk resonator element and is formed on the substrate so as to electrically connect the arcuate contact region to the lower portion of the microdisk resonator element.

In embodiments, the microdisk resonator element is subdivided into a portion that supports a microdisk resonant mode and a portion that supports a micro-ridge resonant mode. The resonator element further includes a taper region that adiabatically converts between said resonant modes.

In other embodiments, the laminar region is of substantially less thickness than a resonant wavelength of light, such that optical mode confinement by the microdisk resonator element is not substantially modified by the presence of the laminar region. Such embodiments do not necessarily include an adiabatic taper, but they offer the advantage of possibly including a heater integrated into the resonator structure.

It is to be understood that both the foregoing general description and the following detailed description are exemplary, but are not restrictive, of the invention.

DETAILED DESCRIPTION

Figure 1A:
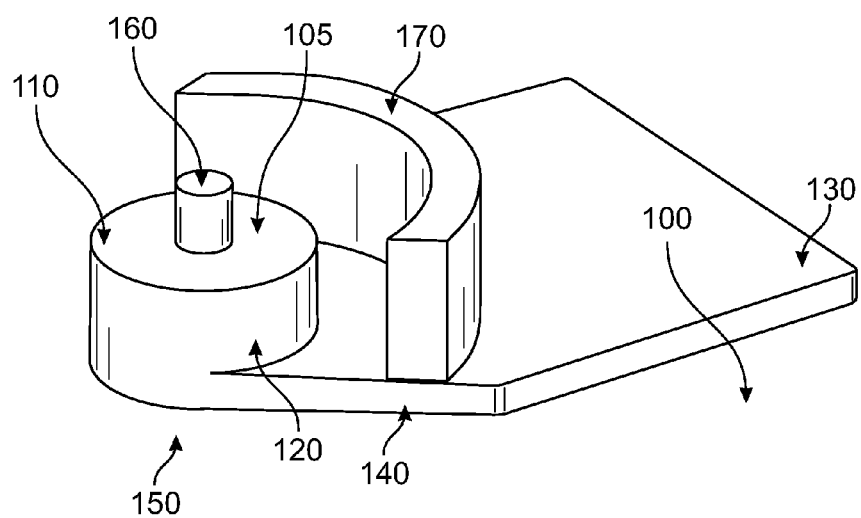
FIG. 1A provides a partially schematic perspective view of a first exemplary embodiment of the present invention, which we refer to as a "top hat resonator".

A first exemplary embodiment, which we refer to as a "top hat resonator", is shown in FIG. 1A. The top hat resonator includes a microdisk resonator that is adiabatically transformed into a ridge resonator. One feature of this exemplary design is that it can effectuate a significant reduction in the series resistance of the resonator, relative to older designs in which an n-type modulator contact and a p-type contact are both centrally located within the disk. In the current state of the art of microdisk modulators, series resistance ultimately limits the electrical bandwidth of the resonator.

As seen in the figure, an exemplary top hat resonator is implemented in silicon on an SOI substrate. The resonator structure 105 comprises portion 110, which is formed on substrate oxide layer 100 and conformed as a portion of a conventional microdisk resonator. Exemplary design details of a silicon microdisk resonator may be gained, for example, from the description of the second exemplary embodiment herein, which is directed to a D-ring resonator. The resonator structure further comprises portion 120, which is formed on silicon pedestal 130 and, although completing the full circular arc of the resonator structure, is conformed to function optically as a ridge resonator. It will be seen that portion 110 stands in relief above oxide layer 100 which underlies, among other things, pedestal layer 130, and that portion 120 stands in relief above pedestal layer 130.

Edge 140 of the pedestal, together with a symmetrically placed edge on the other side of the resonator structure (not visible in the drawing), is seen as tangential and continuous with the bounding part of microdisk portion 110, and as diverging therefrom. The portions 150 of the structure near the tangent points are transition regions in which the confined and resonant optical mode is adiabatically transformed between the profile characteristic of a microdisk resonator and the profile characteristic of a micro-ridge resonator. Specific design parameters for effectuating an adiabatic transition may be found without undue experimentation by exploring the design space using readily available simulation tools. By way of example, the angle between edge 140 and its corresponding opposite edge will typically lie in the range 30-90 degrees. The thickness of the pedestal is preferably less than one-half the total thickness of the disk.

With further reference to the figure, it will be seen that central and peripheral doped silicon contact 160, 170 are respectively formed on a central portion of resonator structure 105 and as a spatially separated arcuate structure on pedestal 130. Contact 160 exemplarily makes contact with the p-doped portion of a vertical pn junction within the resonator structure, and is p+-doped for that purpose. In that event, contact 170 makes contact with the n-doped portion of the same junction via the pedestal, and is n+-doped for that purpose. It should be noted, however, that in alternate implementations, the respective polarities may be reversed, and that a horizontal junction arrangement may be substituted for the vertical junction.

The resonator of FIG. 1A is readily used in conjunction with an optical waveguide, such as a ridge waveguide, to which it is coupled by evanescent coupling. As is well known in the art, such a coupled arrangement can be used, e.g., for purposes of optical switching, modulation, or filtering. Although such a coupled waveguide is not shown in FIG. 1A, the conformation and placement of appropriate such elements will be readily apparent to those skilled in the art.

Figure 1B:
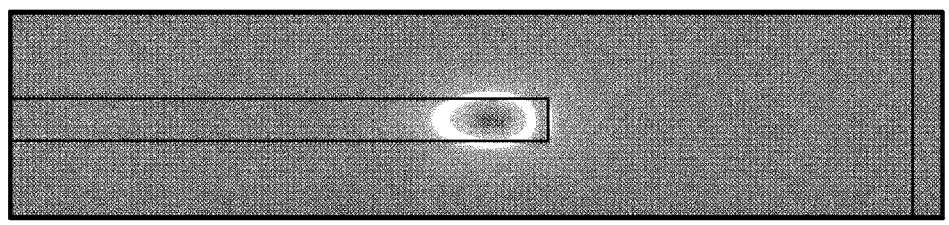
FIGS. 1B and 1C provide an electric field profiles, obtained by numerical simulation, of the resonant mode within respectively an exemplary microdisk resonator and a corresponding micro-ridge resonator. These profiles are provided as a pedagogical aide for an enhanced understanding of the respective modes between which an adiabatic transition is effectuated by the top hat resonator of, e.g., FIG. 1A.
Figure 1C:
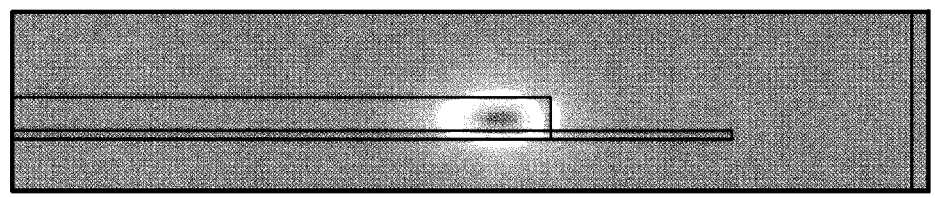

FIG. 1B provides an electric field profile, obtained by numerical simulation, of the resonant mode within an exemplary microdisk resonator of conventional design. FIG. 1C provides an electric field profile, similarly obtained, of a corresponding micro-ridge resonator. As explained above, the inventive top-hat resonator effectuates an adiabatic transition between mode structures of these respective types.

Figure 2:
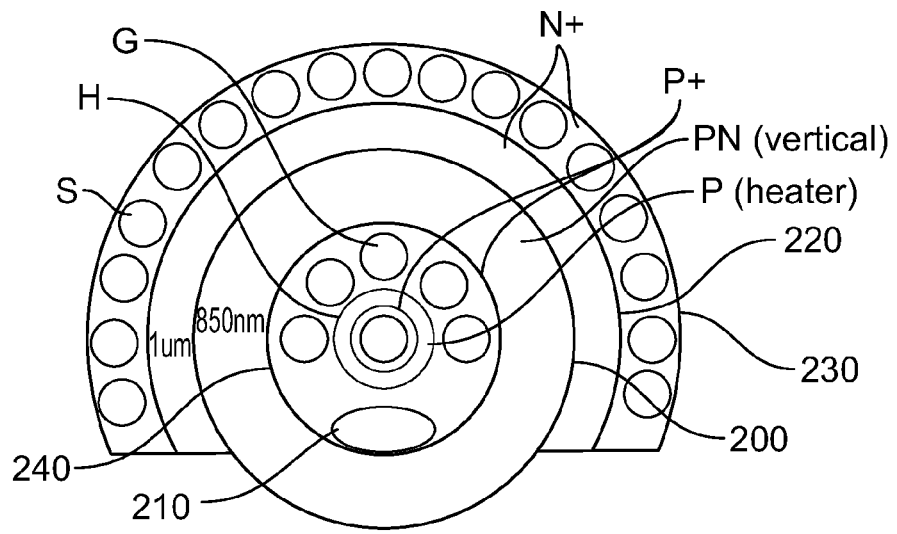
FIG. 2 provides a schematic top-down plan view of a second exemplary embodiment of the present invention, which we refer to as a "D-ring resonator.

A second exemplary embodiment, which we refer to as a "D-ring resonator", is shown in top-down plan view in FIG. 2. The illustrated embodiment includes mode-guiding disk 200, which is exemplarily a silicon disk 250-nm thick and 4.2 µm in diameter formed on an SOI substrate. The upper half of disk 200 is doped p-type and the lower half is doped n-type so that a vertical junction is defined. It should be noted, however, that alternate embodiments may instead employ a horizontal pn junction.

Optical resonance in disk 200 is typically excited by evanescent coupling to a guided wave in a nearby optical waveguide, not shown in the figure. Defined in disk 200 is cutout 210, which those skilled in the art will recognize as a mode-pinning device that may be effective for limiting the resonator to single-mode operation.

Concentric with disk 200 and partially surrounding it is arcuate n+-doped silicon spacer 220, which is exemplarily 50 nm thick and 1 µm wide. Spacer 220 establishes electrical continuity between the n-doped portion of disk 200 and n+-doped silicon contact 230, which is a further arcuate body concentric with and partially surrounding disk 200. Spacer 220 is intended to effectuate the electrical contact while exerting minimal influence on the confinement of the resonant electromagnetic field by disk 220. Some variability in the design of spacer 220 is allowable, as the same purposes may be satisfied using, e.g., widths greater than 1 µm.

The use of spacer 220 is advantageous because it permits the n-type contact, i.e. contact 230, to be situated peripherally. Although peripheral contacts are known in the context of ring-type optical resonators, we are unaware of any previous use thereof for disk-type resonators. Because this arrangement enables the device to be contacted from the outside, bandwidth performance typical of ring designs is achievable, even reaching bandwidths as great as 20 GHz or more.

Because contact 230 is substantially optically isolated from disk 200, its height is not critical and may therefore be determined by factors such as ease of fabrication and ease of making electrical contact rather than by optical constraints.

The angular length of spacer 220 and contact 230 may vary over a substantial range. There are scaling effects that relate the amount of arc to the doping density of disk 200 needed to achieve a given shift $\lambda_{shift}$ in the optical resonant wavelength under bias. The relevant design space can of course be explored through numerical modeling using available modeling tools. More generally, we note that the full width at half-maximum (FWHM) $\lambda_{FWHM}$ of the resonant peak is closely determined by the amount of arc in the disk.

Moreover, the shift in the resonant wavelength varies with the FWHM in proportion to the cube root of the doping density $N_d$:

$$\frac{\Delta \lambda_{shift}}{\Delta \lambda_{FWHM}} \propto \frac{1}{\alpha_{dop} + \alpha_{other}} \cdot N_d^{1/3}.$$

In the preceding equation, $\alpha_{dop}$ represents the optical loss due to dopants, and $\alpha_{other}$ represents the optical loss due to other factors. From the equation it can be seen that reducing the FWHM (by reducing the arc) will result in less dopants being needed to get a similar amount of resonance shift, $\Delta \lambda_{shift}$. As the FWHM and dopant levels change, the disk may have to be moved in relation to the bus waveguide in order to optimize the coupling.

With further reference to the figure, it will be seen that p-type contact 240 is defined as a concentric region situated in the interior of disk 200. The top of contact 240 is at the same level as the top of disk 200. Contact 240 may be formed as a shallow surface region, or it may extend partway or even entirely down to the SOI substrate. It is significant that the conformation of contact 240 can result in less electrical resistance than a comparable ring design, because the corresponding contact in a typical ring design is conformed as a lowered pedestal, which will typically exhibit higher series resistance.

Figure 3:
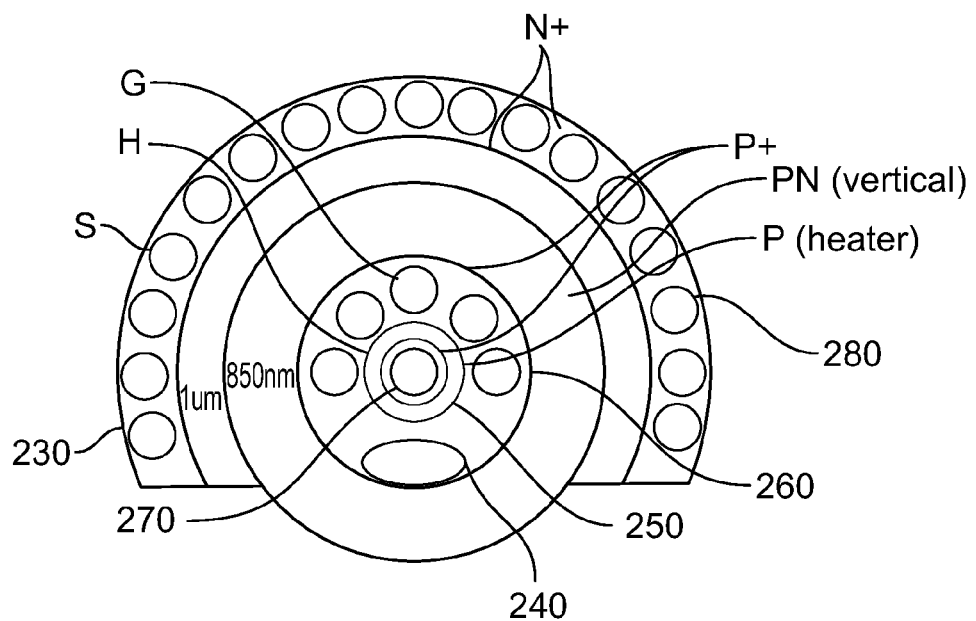
FIG. 3 is a copy of FIG. 2, in which for ease of reference certain reference numerals have been omitted and others have been added. Such reference numerals as are common between FIGS. 2 and 3 call out common elements.

For ease of reference, the drawing of FIG. 2 has been reproduced in FIG. 3, where some elements also called out in FIG. 2 are called out by like reference numerals, while other elements are newly called out by new reference numerals. In some embodiments, it will be advantageous to include a heater for adjusting the optical properties of the device. In fact, a heater is readily integrated into the center portion of disk 200. This is best seen in FIG. 3, where annular p-doped region 250 constitutes the relatively resistive region to be used for ohmic heating. Heater region 250 will typically occupy a shallow surface layer, but this is not critical, and implementations are feasible in which region 250 extends to a substantial depth.

Advantageously, the p-type modulation contact 240 can also serve as the ground contact for the heater. Accordingly, as seen in the figure, the circular array of metal, e.g. tungsten, contacts 260 are provided to make the ground connection for the pn junction and for the heater. Metal, e.g. tungsten, contact 270 provides the other external connection for the heater. The circular array of metal, e.g. tungsten, contacts 280 provides the external connection for n-type contact 230.

As will be understood, our exemplary implementation has a central p-type contact and a peripheral n-type contact. It should be further understood that such a choice of polarities is merely illustrative and although it may be typical, it is not limiting, because interchanging the polarities can also result in an operative device.

It should also be understood that the dimensions provided for our exemplary implementation are merely illustrative and are subject to variation depending on design choices such as material compositions, fabrication techniques, and operating wavelengths. In particular it should be noted that although our example is implemented in silicon, other semiconductor materials can be used in this context, including III-V materials and II-VI materials.

Figure 4:
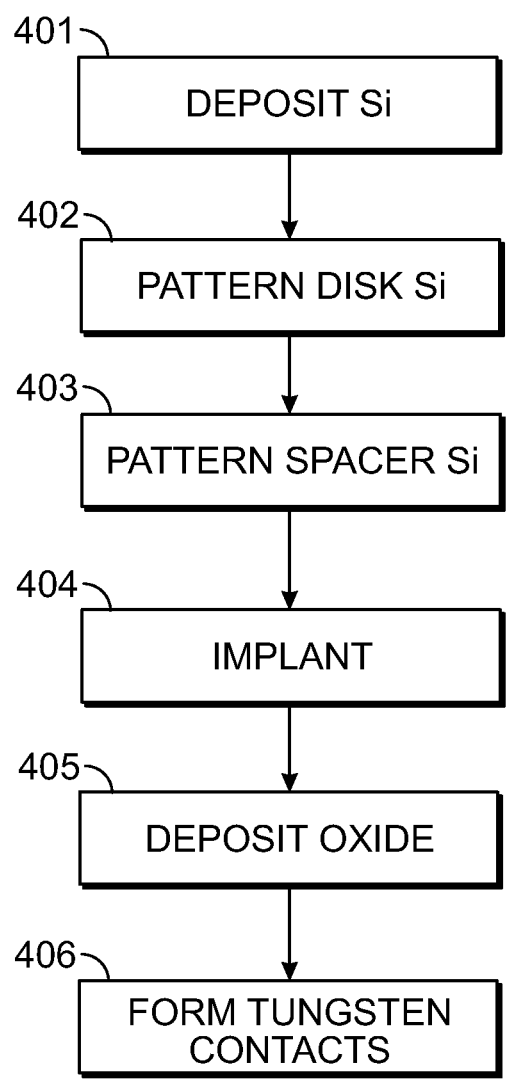
FIG. 4 is a flowchart of an exemplary fabrication sequence for the device of FIGS. 2 and 3.

In an exemplary fabrication sequence for the device of FIGS. 2 and 3 as summarized in FIG. 4, a 250-nm thick layer of silicon is deposited 401 on 3 μm of buried oxide on an SOI substrate. The silicon layer is lithographically patterned and etched 402 to define the features that will become disk 200 and contact 230. A further lithographic patterning and etching step 403 then defines the feature that will become spacer 220. The dopants are then implanted 404 to define the electronic characteristics of each of the respective features of the device. Then oxide is deposited 405 and tungsten contacts are formed 406 according to conventional practices.

What is claimed:

1. An optical device, comprising:
   a microdisk resonator element containing a semiconductor junction;
   an arcuate semiconductor region displaced from and partially surrounding the resonator element;
   a central modulator electrode positioned on a central portion of the resonator element for making contact with one side of the semiconductor junction;
   a peripheral modulator electrode positioned on the arcuate semiconductor region for making contact with the other side of the semiconductor junction; and
   a laminar semiconductor pedestal smaller in thickness than the resonator element and extensive between at least a portion of the resonator element and the arcuate contact region so as to form at least part of an electrical path between the arcuate contact region and its respective side of the semiconductor junction.

2. The optical device of claim 1, wherein the resonator element comprises a first portion supportive of a microdisk optical mode and a second portion supportive of a microridge optical mode.

3. The optical device of claim 2, wherein the resonator element further comprises an adiabatic transition region between said first and second portions.

4. The optical device of claim 3, wherein the first portion stands in relief above a substrate layer that underlies the pedestal, the second portion stands in relief above the pedestal, a pair of edges of the pedestal meet the resonator element at points of tangency that demarcate the first portion from the second portion, and the transition region lies near said points of tangency.

5. The optical device of claim 1, wherein the pedestal is of less thickness than a resonant wavelength of light.

6. The optical device of claim 5, wherein an electric heater is incorporated in a central portion of the resonant element.

\* \* \* \* \*